(12) United States Patent
Huynh et al.

(10) Patent No.: US 8,955,371 B2
(45) Date of Patent: *Feb. 17, 2015

(54) HIGH PRESSURE FRACTURE TESTER

(71) Applicant: M-I L.L.C., Houston, TX (US)

(72) Inventors: Huy Huynh, Houston, TX (US); Robert P. Schlemmer, Kuala Lumpur (MY)

(73) Assignee: M-I LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,421

(22) Filed: May 24, 2013

(65) Prior Publication Data

US 2013/0255369 A1    Oct. 3, 2013

Related U.S. Application Data

(60) Continuation of application No. 13/015,669, filed on Jan. 28, 2011, now Pat. No. 8,448,500, which is a division of application No. 12/050,785, filed on Mar. 18, 2008, now Pat. No. 7,900,504.

(60) Provisional application No. 60/908,097, filed on Mar. 26, 2007.

(51) Int. Cl.
*G01N 33/00* (2006.01)
*E21B 21/08* (2006.01)
(Continued)

(52) U.S. Cl.
CPC .............. *E21B 21/08* (2013.01); *G01N 15/08* (2013.01); *G01N 33/2823* (2013.01)
USPC .......................... 73/61.64; 73/61.41; 73/61.62

(58) Field of Classification Search
USPC .............. 73/37, 38, 49.4, 64.47, 830, 152.01, 73/153.23, 152.18, 61.68, 61.62–61.65; 175/40
See application file for complete search history.

(56) References Cited

U.S. PATENT DOCUMENTS 3,286,510 A    11/1966 Parker
3,289,467 A    12/1966 Parker et al.
3,316,965 A    5/1967 Watanabe
(Continued)

OTHER PUBLICATIONS

Written Opinion for PCT Application No. PCT/US2008/058253, dated Jul. 21, 2008, 3 pages.
(Continued)

*Primary Examiner* — Shane Bomar
*Assistant Examiner* — Kipp Wallace
(74) *Attorney, Agent, or Firm* — Osha Liang LLP

(57) ABSTRACT

A system for testing a drilling fluid including a vessel having a fluid inlet, a filtrate outlet, a fluid outlet, and at least one permeable media disposed within the vessel. The system further including a base fluid container in fluid communication with the fluid inlet, a test fluid container in fluid communication with the fluid inlet, a filtrate container in fluid communication with the filtrate outlet, and a collection container in fluid communication with the fluid outlet. Additionally, the system includes a data acquisition device configured to receive data from at least one of the vessel, the fluid container, the filtrate container, and the collection container. Also, a method for determining sealing characteristics of a drilling fluid including injecting a test fluid having a fluid loss control material from at least fluid container to a vessel, the vessel having a permeable media having two plates disposed to create a variable gap. The methods further including measuring a fracture tip fluid loss through the variable gap and measuring a matrix fluid loss through the permeable media.

16 Claims, 9 Drawing Sheets

(51) Int. Cl.
*G01N 15/08* (2006.01)
*G01N 33/28* (2006.01)

(56) References Cited

U.S. PATENT DOCUMENTS

| | | | |
|---|---|---|---|
| 3,323,593 A | 6/1967 | Foshee et al. | |
| 3,876,006 A | 4/1975 | Messenger | |
| 4,648,264 A | 3/1987 | Freese et al. | |
| 4,691,558 A * | 9/1987 | Vinson et al. | 73/64.41 |
| 4,748,849 A | 6/1988 | Jamison et al. | |
| 4,876,013 A | 10/1989 | Shmidt et al. | |
| 5,309,761 A | 5/1994 | Ravi et al. | |
| 5,488,224 A | 1/1996 | Fagan et al. | |
| 5,987,969 A | 11/1999 | Joseph et al. | |
| 6,055,874 A | 5/2000 | Onan et al. | |
| 6,269,684 B1 | 8/2001 | Maki, Jr. et al. | |
| 6,330,826 B1 | 12/2001 | Meeten et al. | |
| 6,543,276 B2 | 4/2003 | Murphy, Jr. et al. | |
| 6,584,833 B1 | 7/2003 | Jamison et al. | |
| 6,931,916 B2 | 8/2005 | Zamora et al. | |
| 7,284,472 B1 | 10/2007 | Soellner et al. | |
| 7,380,466 B2 | 6/2008 | Deeg | |
| 7,549,320 B2 | 6/2009 | Funkhouser et al. | |

OTHER PUBLICATIONS

International Search Report for PCT Application No. PCT/US2008/058253, dated Jul. 21, 2008, 3 pages.
Supplementary European Search Report issued in corresponding European Application No. 08799665.8 dated Jun. 2, 2014 (7 pages).

* cited by examiner

HIGH PRESSURE FRACTURE TESTER

CROSS-REFERENCE TO RELATED APPLICATIONS

This is a continuation application and claims benefit under 35 U.S.C. §120 to U.S. patent application Ser. No. 13/015,669, filed Jan. 28, 2011, now U.S. Pat. No. 8,448,500, issued May 28, 2013, which is a divisional application of U.S. patent application Ser. No. 12/050,785, filed on Mar. 18, 2008, now U.S. Pat. No. 7,900,504, issued Mar. 8, 2011, which claims priority, pursuant to 35 U.S.C. 119(e) to U.S. Provisional Patent Application No. 60/908,097, filed Mar. 26, 2007. These applications are expressly incorporated by reference in their entirety.

BACKGROUND

1. Field of the Disclosure

The present disclosure generally relates to systems and methods for testing drilling fluids for drilling operations. More particularly, the present disclosure relates to methods and systems for determining sealing characteristics of fluid loss control materials and optimizing drilling fluids using such particles.

2. Background Art

During the drilling of a wellbore, various fluids are typically used in the well for a variety of functions. The fluids may be circulated through a drill pipe and drill bit into the wellbore, and then may subsequently flow upward through wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

In most rotary drilling procedures the drilling fluid takes the form of a "mud," i.e., a liquid having solids suspended therein. The solids function to impart desired rheological properties to the drilling fluid and also to increase the density thereof in order to provide a suitable hydrostatic pressure at the bottom of the well. The drilling mud may be either a water-based or an oil-based mud.

Drilling muds may consist of polymers, biopolymers, clays and organic colloids added to a water-based fluid to obtain the required viscosity and filtration properties. Heavy minerals, such as barite or calcium carbonate, may be added to increase density. Solids from the formation are incorporated into the mud and often become dispersed in the mud as a consequence of drilling. Further, drilling muds may contain one or more natural and/or synthetic polymeric additives, including polymeric additives that increase the rheological properties (e.g., plastic viscosity, yield point value, gel strength) of the drilling mud, and polymeric thinners and flocculents.

Polymeric additives included in the drilling fluid may act as fluid loss control agents. Fluid loss control agents, such as starch, prevent the loss of fluid to the surrounding formation by reducing the permeability of filter cakes formed on the newly exposed rock surface. In addition, polymeric additives are employed to impart sufficient carrying capacity and thixotropy to the mud to enable the mud to transport the cuttings up to the surface and to prevent the cuttings from settling out of the mud when circulation is interrupted.

As such, many drilling fluids may be designed to form a thin, low-permeability filter cake to seal permeable formations penetrated by the drill bit. The filter cake is essential to prevent or reduce both the loss of fluids into the formation and the influx of fluids present in the formation. Upon completion of drilling, the filter cake may stabilize the wellbore during subsequent completion operations such as placement of a gravel pack in the wellbore. Filter cakes often comprise bridging particles, cuttings created by the drilling process, polymeric additives, and precipitates. One feature of a drilling fluid is to retain these solid and semi-solid particles as a stable suspension, free of significant settling over the time scale of drilling operations.

Once the drilling fluid is lost into the formation, it becomes difficult to remove. Calcium and zinc-bromide brines can form highly stable, acid insoluble compounds when reacted with the formation or substances contained therein. This reaction may reduce the permeability of the formation to any subsequent out-flow of the targeted hydrocarbons. The most effective way to prevent such damage to the formation is to limit fluid loss into the formation.

Thus, providing effective fluid loss control is highly desirable to prevent damaging the formation in, for example, completion, drilling, drill-in, displacement, hydraulic fracturing, work-over, packer fluid emplacement or maintenance, well treating, or testing operations. In certain drilling environments, the formation may be exceptionally prone to damage from fluid loss. Examples of such drilling operations may include depleted zone drilling.

Depleted drilling zones may be especially prone to fractures (i.e, cracks and disruptions in a formation that may be either naturally formed or induced). Fracturing during the drilling operation, also known as induced fracturing, typically occurs in permeable rocks such as sandstone and carbonates or within impermeable rock typified by shale formations. Induced fracturing is of particular concern when drilling into depleted zones where a drop in pore pressure is anticipated as the reserves decline. In these situations, drilling then becomes more of a technical challenge as the mud weight required to support a section may exceed the tensile strength, or fracture resistance, of the formation. This in turn could lead to increased drilling fluid losses and increased well costs.

In order to prevent fluid loss and increased well costs a number of tests and equipment for testing drilling fluids and formation for fluid loss and sealing characterstics have been developed. Previous work on the fracture studies resulted in the development of an apparatus that could mimic fractures in impermeable rock. This particular equipment included an opposed piston design that used two matched 2.5-inch diameter corrugated aluminum platens to simulate formation fracture faces. The fracture gap could be set using three screws. Furthermore, the fracture faces were sandblasted in order to increase the level of surface irregularities and friction allowing for better particle adhesion and to encourage bridging.

The operation of the impermeable fracture test apparatus involved pumping a test fluid containing fluid loss control materials through the open fracture of a fracture cell and into a fracture tip accumulator cell. The test fluid was pumped at a constant flow rate while maintaining constant fracture tip and fracture closure pressures. The effects of the fluid and/or fluid loss control material on a fracture of pre-determined width could then be determined by monitoring the mud pressure, which is variable and dependent upon the quality of fracture seal.

While the test apparatus allowed an operator to gain some minimal understanding of how fluid loss control materials contributed to sealing impermeable fractures, the equipment was limited to only measuring a fluid loss at the fracture tip.

Accordingly, there exists a continuing need for systems and methods of testing and optimizing drilling fluids and/or fluid loss control materials for drilling in permeable and impermeable formation.

SUMMARY OF THE DISCLOSURE

In one aspect, embodiments disclosed herein relate to a system for testing a drilling fluid including a vessel having a fluid inlet, a filtrate outlet, a fluid outlet, and at least one permeable media disposed within the vessel. The system further including a base fluid container in fluid communication with the fluid inlet, a test fluid container in fluid communication with the fluid inlet, a filtrate container in fluid communication with the filtrate outlet, and a collection container in fluid communication with the fluid outlet. Additionally, the system includes a data acquisition device configured to receive data from at least one of the vessel, the fluid container, the filtrate container, and the collection container.

In another aspect, embodiments disclosed herein relate to a method for determining sealing characteristics of a drilling fluid including injecting a test fluid having a fluid loss control material from at least fluid container to a vessel, the vessel having a permeable media having two plates disposed to create a variable gap. The methods further including measuring a fracture tip fluid loss through the variable gap and measuring a matrix fluid loss through the permeable media.

In another aspect, embodiments disclosed herein relate to a method for optimizing a drilling fluid including injecting a drilling fluid having a first fluid loss control material particle size into a vessel, wherein the vessel has a permeable media having two plates that are disposed to create a variable gap. The method further including measuring a fracture tip fluid loss through the variable gap and measuring a matrix fluid loss through the permeable medial. Additionally, the method includes determining a sealing parameter based on the fracture tip fluid loss and the matrix fluid loss and adjusting the particle size based on the fluid parameter.

Other aspects and advantages of the disclosure will be apparent from the following description and the appended claims.

DETAILED DESCRIPTION

The present disclosure generally relates to systems and methods for testing drilling fluids for drilling operations. More particularly, the present disclosure relates to methods and systems for determining sealing characteristics of fluid loss control materials and optimizing drilling fluids using such particles.

Embodiments of the present disclosure described herein include a testing system for determining the sealing characteristics of drilling fluids, including both oil- and water-based fluids, as may be used in drilling earth formations. The types of formations discussed below generally include permeable formations such as sandstone and carbonates, however, the present disclosure may also find use when testing drilling fluids used while drilling impermeable formations such as shale. Those of ordinary skill in the art will appreciate that the type of formation being tested and the specific fluids discussed below are not a limitation on the scope of the present disclosure. As such, all discussed examples are merely exemplary, and the systems of testing and methods of determining sealing characteristics and optimizing drilling fluids are exemplary as well.

Figure 1:
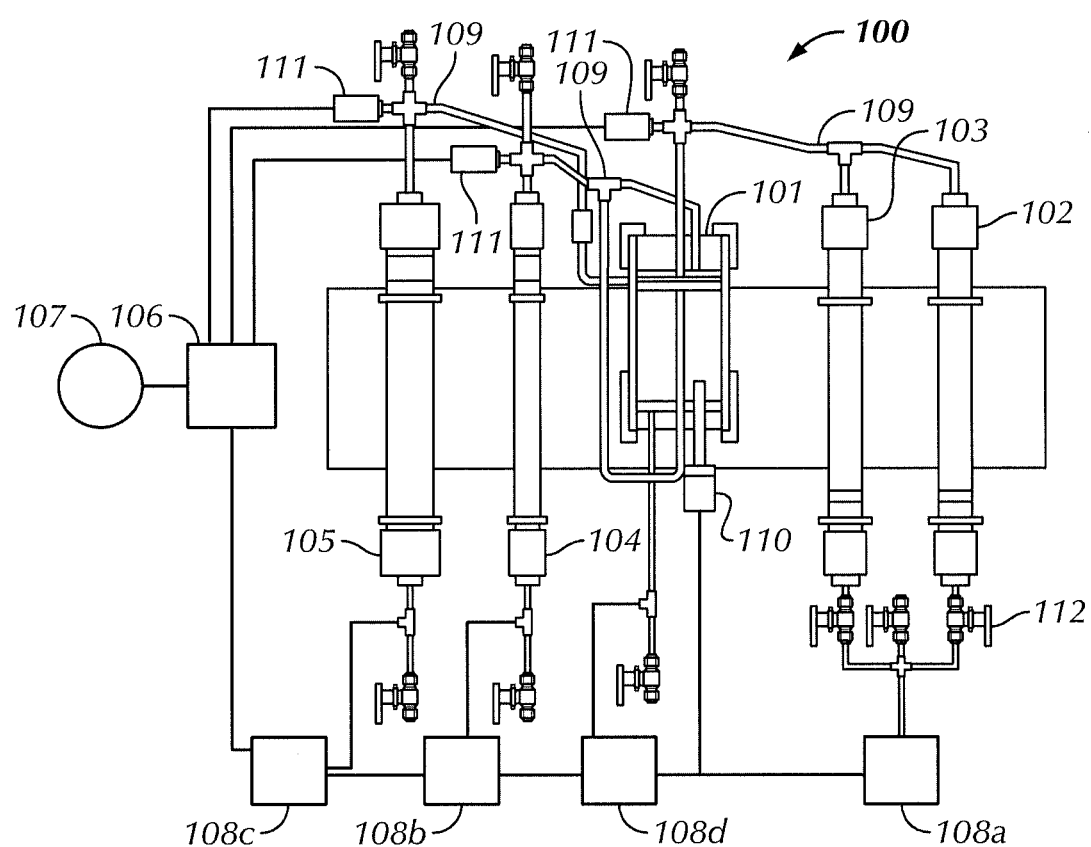
FIG. 1 shows a system for testing a drilling fluid in accordance with embodiments of the present disclosure.

Referring to FIG. 1, a system 100 for testing a drilling fluid in accordance with embodiments of the present disclosure is shown. In this embodiment, system 100 includes a testing vessel 101 and several fluid containers 102, 103, 104, and 105. System 100 also includes a data acquisition system 106, a computer 107, and a series of pumps 108.

More specifically, system 100 includes a base fluid container 102 and a test fluid container 103 in fluid communication with vessel 101. Containers 102 and 103 may include any type of containers used to contain drilling fluid, and as such, may include plastic, steel, or composite containers. Those of ordinary skill in the art will appreciate that because the system is pressurized, the containers must be able to handle the requisite pressure requirements of system 100. Likewise, the fluid connections providing fluid communication between containers 102 and 103 and vessel 101 must also be able to handle pressure requirements of the system, and as such, appropriate fluid lines 109 may include steel lines, reinforced plastic lines, and other lines as known to those of ordinary skill in the art.

In this embodiment, a first pump 108a is used to pressurize system 100 by providing a pressure to base fluid container 102 and test fluid container 103. A base fluid is stored in base fluid container 102, and a test fluid is stored in test fluid container 103. Pump 108a is used to deliver both the base fluid and the test fluid, as required by the testing operation, to vessel 101. In one aspect, pump 108a may include a syringe pump, however, those of ordinary skill in the art will appreciate that other types of pumps may be used to inject a fluid from containers 102 and 103 to vessel 101.

A filtrate container 104 is used to collect a filtrate from vessel 101 during the testing. Similar to containers 102, and 103, filtrate container 104 may also include any type of container used to hold drilling fluids, and as such, may include steel or plastic containers. Filtrate container 104 is also fluidly connected to vessel 101 via fluid lines 109, as described with respect to containers 102 and 103 above. In this embodiment, a second pump 108b provides a back pressure to the matrix (not independently illustrated) of vessel 101. This pump may also be used to record the volume of filtrate lost through the matrix as accumulated in filtrate container 104. In one aspect, second pump 108*b* may include a syringe pump, however, other pumps may be used that create a back pressure to the fracture tip, as described above.

A collection container 105 is used to collect a fluid from vessel 101 during the testing. Collection container 105 may also include any type of container used to hold drilling fluids, and as such, may include steel or plastic containers. Collection container 105 is also fluidly connected to vessel 101 via fluid lines 109, as described with respect to containers 102, 103, and 104 above. In this embodiment, a third pump 108*c* provides a back pressure to the fracture tip (not independently illustrated) of vessel 101. This pump may also be used to record the volume of fluid lost through the fracture tip as accumulated in filtrate container 104. In one aspect, third pump 108*c* may include a syringe pump, however, other pumps may be used that create a back pressure to the fracture tip, as described above.

A fourth pump 108*d* is connected to vessel 101 to control a constant fracture width of media plates (not shown) disposed in vessel 101. Fourth pump 108*d* is controlled, in this embodiment, by a linear transducer 110 that is operatively connected to vessel 101 and fourth pump 108*d* to maintain a constant fracture wide of media plates (not shown) based on a reading of linear distance between the media plates. Said another way, linear transducer 110 is used to control the fracture closure pressures. Those of ordinary skill in the art will appreciate that in other embodiments, linear transducer 110 may not be required, and the fracture closure pressures may be recorded by other types of transducers, pressure gauges, or other devices as known to those of skill in the art. In one aspect, third pump 108*d* may include a syringe pump, however, other pumps may be used that provide a pressure to vessel 101 and/or transducer 110 to control and/or measure a pressure inside vessel 101.

Those of ordinary skill in art will appreciate that in other systems, a single pump or other configurations of pumps may provide the requisite pressures to test a drilling fluid. As such, the precise configuration of pumps 108 described in FIG. 1 is not a limitation on the scope of the present disclosure.

System 100 also includes a plurality of sensors 111 that may be used to measure, inter alia, pressures, temperatures, densities, conductivities flow rates, flow levels, or other parameters of system 100 or of drilling fluids being tested. Thus, sensors 111 may be used to collect data or to determine a condition of system 100. In this embodiment, sensors 111 are operatively connected to data acquisition system 106. Data acquisition system 106 may include any device used to collect, document, or analyze data from system 100. Examples of data acquisition systems 106 that may be used in aspects of the present disclosure include analog-to-digital converters and digital-to-analog converters. Thus, embodiments in certain embodiments, data acquisition system 106 may receive a digital and/or analog input/output from sensors 111, pumps 108, or directly from another component of system 100, collect and/or analyze the data, and in certain embodiments, transfer the data to a computer 107 for further analyzing. Examples of methods of transferring the data from data acquisition system 106 to computer 107 may include, for example, via a USB (universal serial bus), parallel ports, serial communication ports, direct data acquisition plug-in boards, or remote terminal connections. Thus, in certain embodiments, data acquisition system 106 may be directly or indirectly configured to transfer data to computer 107.

Likewise, computer 107 may be used to send instructions to data acquisition system 106, sensors 111, pumps 108, or other components of system 100. Examples of such instructions may include instructions to control an operational parameter, such as, a pressure, a flow rate of a fluid, a distance between media plates, or instructions to request additional data from a component of system 100. Such instructions may be sent from computer 107 either through data acquisition system 106 or, in certain embodiments, directly to an individual component of system 100. Those of ordinary skill in the art will appreciate that computer 107 may be used to collect data, analyze data, and/or to control the testing.

Additionally, computer 107 may be used to render visual representations of collected and analyzed data. Visual representations may include the generation of data tables, numerical representations, graphical representations, or other forms of displaying data. Examples of such visual representations will be discussed in greater detail below.

Other components of system 100 may include a plurality of valves 112, which may be controlled via data acquisition system 106, computer 107, or otherwise manually actuated to control an operational parameter of system 100. Those of ordinary skill in the art will appreciate that any number of valves, valve types, and location of such valves will vary according to the design of system 100. However, generally, it may be beneficial to have valves in locations to control both the flow of fluids through system 100 and the pressure of portions of system 100. Furthermore, those of ordinary skill in the art will appreciate that other design variations to system 100 may be possible that include additional components such as, for example, multiple computers 107, data acquisition systems 106, multiple test vessels 101, additional fluid containers 102, 103, 104, and 105, or additional sensors 111 including other measuring devices.

While system 100 has been discussed generally above, the construction and components parts of vessel 101 will be discussed in detail below so that the operation and testing conditions system 100 provides for is more clearly understood.

Figure 2:
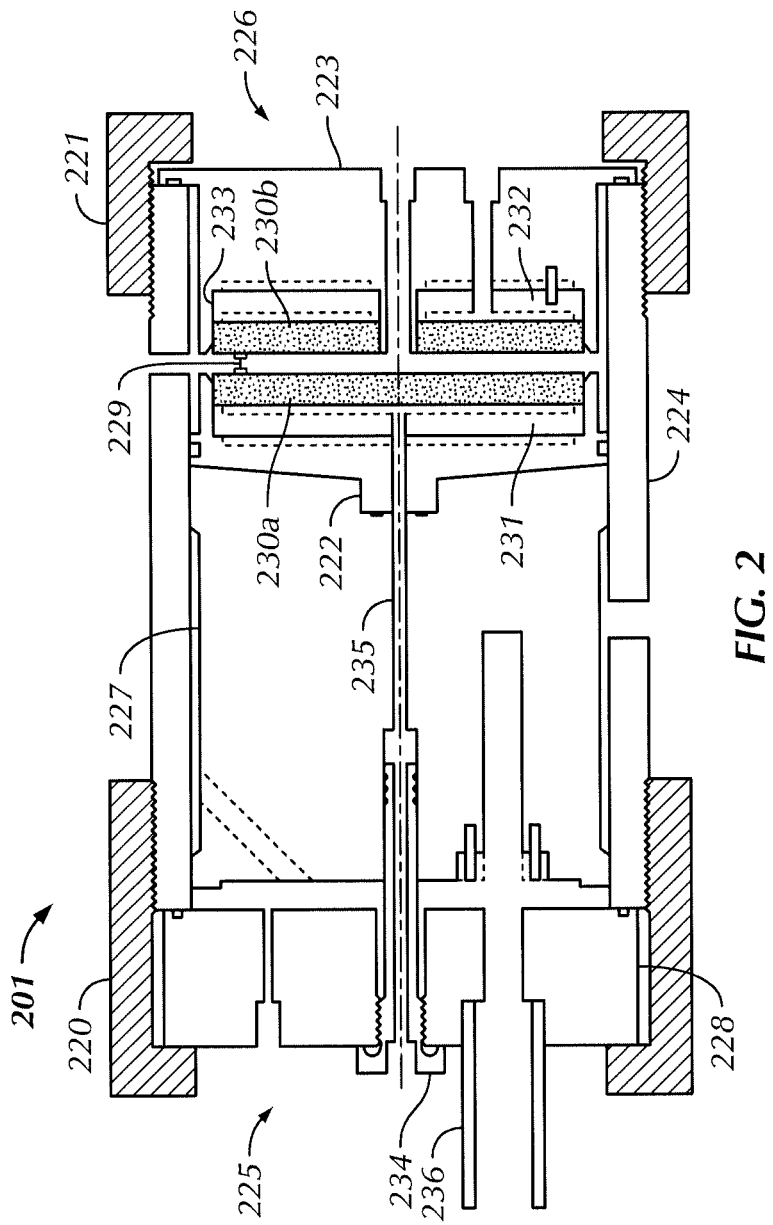
FIG. 2 shows a cross-section view of a vessel according to embodiments of the present disclosure.

Referring to FIG. 2, a cross-section view of vessel 201 according to embodiments of the present disclosure is shown. In this embodiment, vessel 201 includes a pressure chamber 224, an upper cap 220, and a lower cap 221. As illustrated, pressure chamber 224 is sealed on a first end 225 by upper cap 220 and sealed on a second end 226 by lower cap 221. A material that may be used to construct pressure chamber 224, upper cap 220, and lower cap 221 includes, for example, 4130 alloy steel. However, those of ordinary skill in the art will appreciate that other materials may be used that are both sealable and that withstand the pressure requirements of vessel 201. Examples of types of sealing engagement between upper cap 221, lower cap 220, and pressure chamber 224 include threadable and/or slidably engaging connections. In a threadable connection, an inner diameter of upper cap 221 or lower cap 220 may be configured to threadably engage an outer diameter of pressure chamber 224 to provide a sealed system that prevents the escape of fluids and gasses. In a slidably engaging system, pressure chamber 224 may include ratcheting ends (not shown) that slidably engage ratchet ends of upper cap 221 or lower cap 220. To further enhance the sealability of vessel 201, thereby preventing the escape of gases and fluids therefrom, additional components may be used including, for example, one or more seals disposed along the outer diameter of pressure chamber 224. Those of ordinary skill in the art will appreciate that the method of constructing the body of vessel 201 is exemplary, and not a limitation on the scope of the present disclosure.

Vessel 201 also includes a piston 227 disposed inside vessel 201 between an upper pressure plate 228 and an upper sleeve 222. Upper pressure plate 228, in one embodiment, may be constructed from 304 grade stainless steel and forms a sealing barrier between upper cap 220 and piston 227. Piston 227 is slidably disposed inside pressure chamber 224, and is movable to control a variable gap 229 between media plates 230, as will be discussed below. Piston 227 may be constructed from, for example, 7075 grade aluminum, and may have inner chamber for the insertion of linear transducers (not shown) therein.

In this embodiment, piston 227 is disposed between upper pressure plate 228 and upper sleeve 222. Upper sleeve 222 is constructed from 304 grade stainless steel and is disposed between a top spacer 231 and a top media plate 230*a*. Top spacer 231 is constructed from 2011 grade aluminum and provides a barrier between upper sleeve 222 and media plate 230*a*.

Additionally, a bottom media plate 230*b* is disposed opposed top media plate 230*a* and proximate a bottom spacer 232. Bottom spacer 232 is constructed from 2011 grade aluminum and forms a barrier between bottom media plate 230*b* and a lower sleeve 223. Lower sleeve 223 is disposed inside pressure chamber 224 and forms a sealing engagement with bottom cap 221.

In this embodiment top media plate 230*a* is shown separated from bottom media plate 230*b* such that a variable gap 229 is formed therebetween. Variable gap 229 defines the distance top and bottom media plates 230*a* and 230*b* are apart for a given test. Thus, in one embodiment, variable gap 229 may be substantially touching thereby forming a small variable gap, while in other embodiments, variable gap 229 may be a specified distance apart, thereby forming an incrementally larger variable gap 229. Those of ordinary skill in the art will appreciate that variable gap 229 may be adjustable by moving piston 227 inside pressure chamber 224 to bring media plates 230 closer together. Moving piston 227 may occur by, for example, tightening the engagement of upper cap 220 with upper pressure plate 228. In other embodiments, variable gap 229 may be controlled by adjusting a ratcheting mechanism between upper sleeve 222 and lower sleeve 223, such as ratcheting member 233. Those of ordinary skill in the art will appreciate that the mechanism used to control variable gap 229 is not a limitation on the scope of the present disclosure; rather, the ability to control variable gap 229 may further increase the range of fluids vessel 201 may test.

Media plate 230, disposed within pressure chamber 224, may be any type of media plate capable of testing a drilling fluid. Examples of media plates may include porous soapstone plates, including 175 micro plates that allow a flow of fluids therethrough. Lower porosity media plates 230 may also be used in certain embodiments to simulate lower porosity formation. Those of ordinary skill in the art will appreciate that the exact porosity of media plates 230 may be varied according to the type of formulation being simulated. For example, if a drilling operator wanted to test a drilling fluid for use in a lower permeable formation, the porosity of media plate 230 may be decreased to replicate such a formation. However, for more permeable formation types, the porosity may be increased to more accurately simulate the type of formation, in which the drilling fluid is used. Additionally, media plate 230 may include formation replications including soapstones, as discussed above, actual cut earth formation, porous paper based media, or media forged from, for example, metals.

In one embodiment, vessel 201 also includes a filtrate pipe 234 disposed to remove a filtrate that escaped through media plate 230. For example, in operation, fluid in the form of a filtrate may pass through media plates 230 through a channel 235 and exit vessel 201 through filtrate pipe 234 Thus, in one embodiment, filtrate pipe 234 may extend through upper pressure plate 228, piston 227, upper sleeve 222, and top spacer 231 to form a channel 235 to media plate 230*a*. Additionally, channel 235 may extend to receive a filtrate that passes through media plate 230*b* by extending to bottom spacer 232.

Vessel 201 may also include a transducer extender 236 that extends through upper pressure plate 228 and into piston 227, such that a transducer (not shown) may be inserted therein for obtaining a linear distance between media plates 230. As described above, the linear distance obtained my be used to control the fracture closure pressure of vessel 201, and otherwise determine and regulate variable gap 229. For example, if a lower than expected pressure is indicated by the transducer, that could be a sign that back pressure in the system is too low and variable gap 229 is expanding. Thus, an operator or a computer could adjust a pump pressure to increase back pressure to vessel 201 thereby decreasing variable gap 229 to a preferred distance. Alternatively, if a measured linear distance indicates that variable gap 229 is lower than desired, a back pressure could be decreased to increase variable gap 229, thereby obtaining a desired testable condition. Those of ordinary skill in the art will appreciate that variable gap 229, the porosity of media plates 230, and construction of vessel 201 may be varied, and still be within the scope of the present disclosure.

Figure 3A:
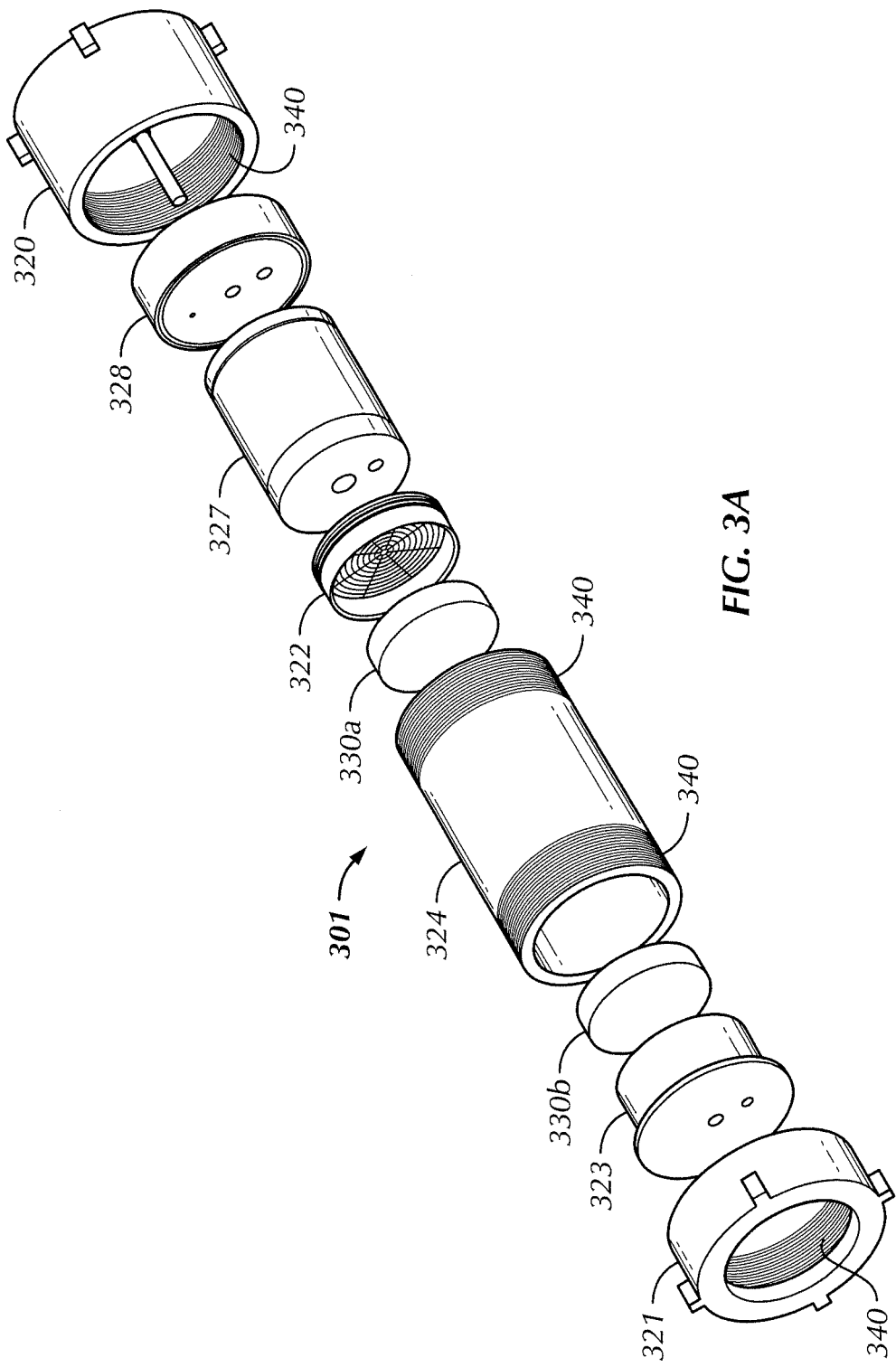
FIG. 3A shows an exploded view of a vessel according to embodiments of the present disclosure.

Referring to FIG. 3A, an exploded view of a vessel 301 according to embodiments of the present disclosure is shown. In this embodiment vessel 301 is illustrated including an upper cap 320, a pressure chamber 324, and a bottom cap 321. A plurality of threads 340 are disposed along the inner diameter of upper cap 320, along the outer diameter of pressure chamber 324, and along the inner diameter of bottom cap 321, such that when threadably connected, vessel 301 is substantially sealed.

Vessel 301 also includes an upper pressure plate 328 disposed between upper cap 320 and a piston 327. Piston 327 is disposed between upper cap 320 and an upper sleeve 322 disposed within pressure chamber 324. Similarly, vessel 301 includes a bottom sleeve 323 disposed between bottom cap 321 and upper sleeve 322. Between upper sleeve 322 and bottom sleeve 323 an upper media plate 330*a* and a lower media plate 330*b* may be placed.

Figure 3B:
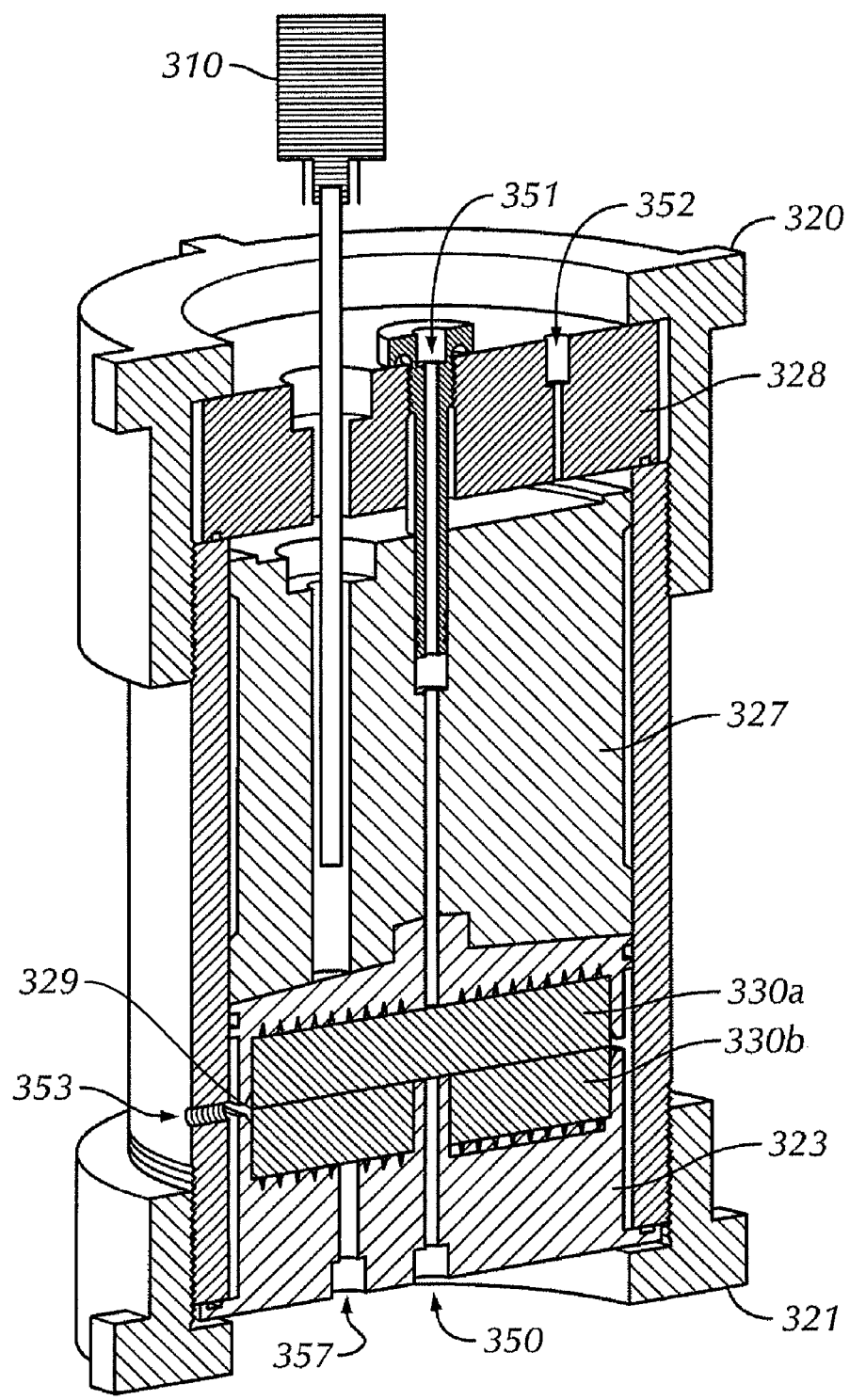
FIGS. 3B-3C show a cross-sectional assembled view of the vessel from FIG. 3A according to embodiments of the present disclosure.
Figure 3C:
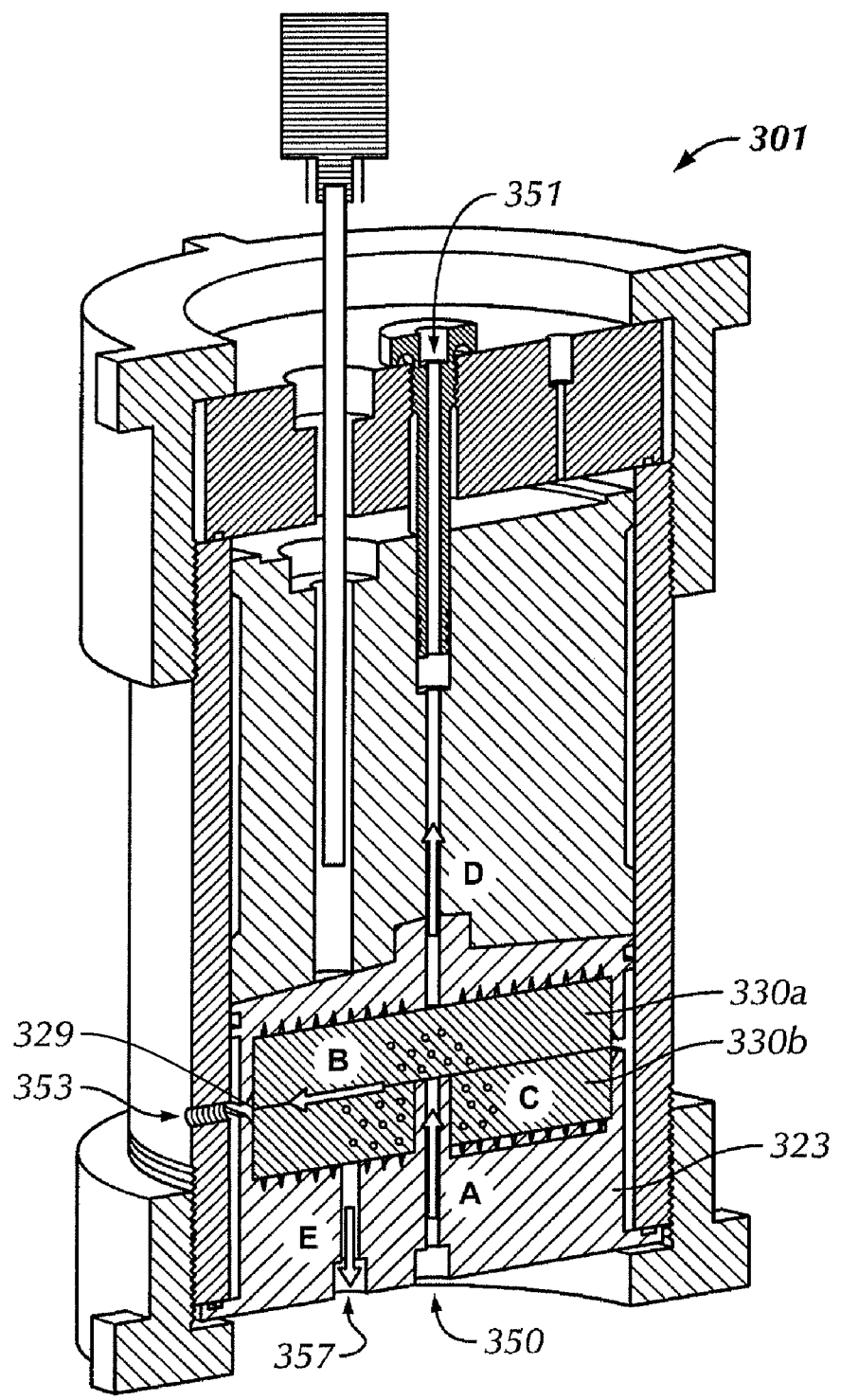

Referring to FIGS. 3B and 3C, a cross-sectional assembled view of vessel 301 from FIG. 3A according to embodiments of the present disclosure is shown. For brevity, like numbers in FIGS. 3A and 3B represent like parts. In this illustration, vessel 301 is shown including a fluid inlet 350 and two filtrate outlets 351. Vessel 301 also includes a hydraulic pressure inlet 352, a fluid outlet 353, and is illustrated including an inserted linear transducer 310.

Operationally, as a drilling fluid is pumped into fluid inlet 350 along path A it contacts media plates 330*a* and 330*b*, representative of a selected formation. A certain portion of the fluid may then be forced out of variable gap 329, generally following a path of least resistance, along path B, and exit vessel through fluid outlet 353. However, as variable gap 329 is filled with fluid loss control material, the path of least resistance may cease to be exiting vessel 301 via fluids outlet 353. Instead, a portion of the fluid may permeate media plates 330 following path C and exit vessel 301 following paths D and E via filtrate outlets 351.

The fluid exiting through fluid outlet 353 is also considered fracture tip fluid loss because variable gap 329 may represent a fracture in a formation. Thus, as fluid loss control materials begin to block the fluid from exiting the fracture tip, thereby sealing the fracture, the substantially constant pressure from the injected fluid may cause the fluid to permeate into the media plates 330. The fluid that permeates media plates 330 and exits vessel 301 via filtrate outlet 351 is referred to as matrix fluid loss. Matrix fluid loss represents the fluid lost as drilling fluids escapes into, for example, a permeable formation or a permeable filter cake, during a drilling operation. However, those of ordinary skill in the art will appreciate that as fluid loss control material begins to fill and block the porous media plates 330, the loss of fluids flowing therethrough may decrease. Said another way, as more of the pores of media plates 330 become blocked, a matrix fluid loss may decrease. As such, in certain embodiments, data my be collected by measuring the amount of fracture tip fluid loss and matrix fluid loss, and subsequently determining how effective fluid loss control materials are at treating a fractured and/or specified porous formation.

Figure 3D:
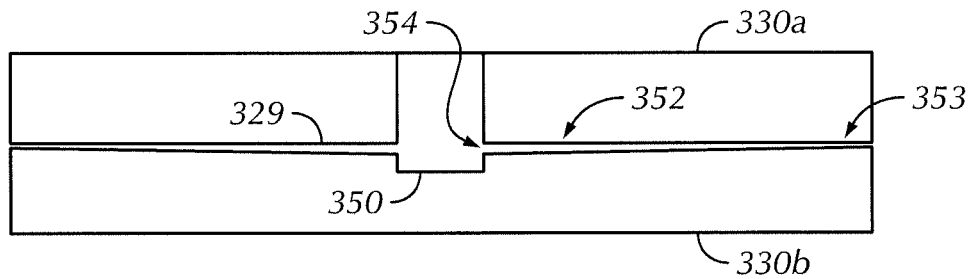
FIG. 3D shows a cross-sectional view of a fracture according to embodiments of the present disclosure.

Referring briefly to FIG. 3D, a cross-section of an alternate variable gap 329 according to embodiments of the present disclosure is shown. In this embodiment, variable gap 329 is adjusted such that the fracture space between the media plates has a tapered configuration. In such an embodiment, a fluid is injected into a fluid inlet 350 and enters variable gap 329 located between a top media plate 330a and a bottom media plate 330b. The fluid may then flow through variable gap 329 from a relatively wide section 352 (e.g., a 1000 micron section) through variable gap 329 to a fluid outlet 353 located at a relatively thin section (e.g., a 500 micron section). Those of ordinary skill in the art will appreciate that the tapered widths of variable gap 329 may vary according to a type of formation being modeled or according to the requirements of a test.

Additionally, fluid inlet 350 may be adjustable such that the amount of fluid entering variable gap 329 may also be controlled. In one aspect, fluid inlet 350 may be adjustable 354 within a range of, for example, 1000-3000 microns. Such an adjustable fluid inlet 354 may further increase the variables tested during the systems and methods disclosed herein. Examples of variables that may be tested include additional fracture tip pressure measurements, flow rates, and fluid loss rates. Those of ordinary skill in the art will appreciate that while static and tapered variable gap geometries have been discussed herein, alternate configurations such as, for example, corrugated variable gap/fracture geometry, are also within the scope of the present disclosure. Those of ordinary skill in the art will further appreciate that the methods of adjusting variable gap 329 in a tapered or corrugated design may include adjusting geometries of media plates 330a or 330b, as illustrated, or changing another aspect of vessel design such as changing a geometry of a spacer or a pressure chamber.

Operationally, embodiments of the present disclosure may be used to test and determine sealing characteristics of a drilling fluid. Subsequently, the sealing characteristics, and the data obtained from the testing, may be used to optimize a drilling fluid for drilling through a given formation.

Figure 4:
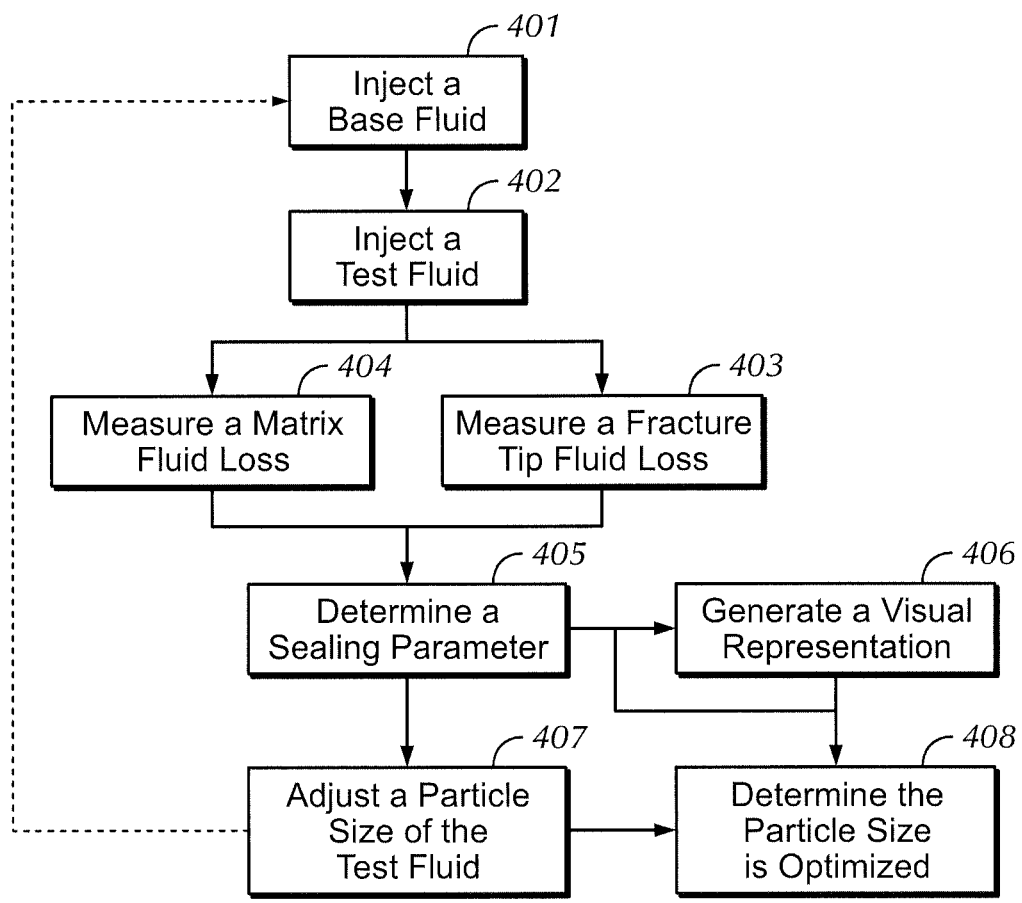
FIG. 4 shows a flow chart of a method for determining sealing characteristics and for optimizing a drilling fluid.

Referring to FIG. 4, a flow chart of a method for determining sealing characteristics and for optimizing a drilling fluid is shown. In this embodiment, a base fluid generally including, for example, a water-based or oil-based fluid of a known viscosity and known properties, is injected 401 from a fluids container into a vessel, as described above. The base fluid may be used to determine a base flow rate and to pressurize the equipment for the test fluid.

After the system is pressurized by injecting 401 the base fluid, a test fluid is injected 402 from a test fluid container. The test fluid may include a water-based or oil-based fluid including fluid loss control material of a known particle size. Examples of fluid loss control materials that may be tested includes sized graphite, barite, calcium carbonate, ground nut, and other fluid loss control material as are known to those of ordinary skill in the art. The test fluid generally contains a known concentration of fluid loss control material and is injected 402 under a known pressure. As such, a rate flow of the test fluid though the vessel will be known. Injection 402 continues under known pressure and flow rate conditions, and the fluid is substantially continuously injected into a fluids inlet of the vessel.

Inside the vessel, the fluid contacts the media plates, and by following a path of least resistance travels through a variable gap between media plates, as described above. As the fluid passes through the variable gap, the fluid begins to adhere to the sidewalls of the media plates, and the fluid loss control material begins to block fluid flow through the variable gap. However, some of the fluid may pass through fluid outlet and into a collection container. The volume of fluid flowing into the collection container may then be measured 403, and as such, a measured fracture tip fluid loss is determined. The amount of fluid lost through the variable gap represents a fracture tip fluid loss, as described above, and may be used later in the process for determining sealing properties of fluid loss control material and/or drilling fluids in general.

Contemporaneous with the measuring 403 of a fracture tip fluid loss, a portion of the drill fluid including fluid loss control material entrained therein may be forced under pressure into the media plates. Because the media plates are porous, a portion of the fluid may pass through the media plates, exit the vessel through filtrate outlets, and collect in a filtrate container. As the fluid loss control material passes through the porous media plates, the flow of fluids therethrough may decrease due to the porous structure of the media plates becoming blocked by the fluid loss control material. However, a portion of the fluid may pass through the media plates and be collected in the filtrate container, as discussed above. The volume of fluid flowing into the filtrated collection container may then be measured 404, and as such, a measured matrix fluid loss obtained. The amount of fluid lost though the media represents matrix fluid loss, as described above, and may be used later in the testing to determine sealing properties of fluid loss control materials and/or drilling fluids in general.

As the measurements of fracture tip fluid loss and matrix fluid loss are determined, a data acquisition system, as described above, may be recording and collecting data from the system. Examples of such collected data may include the pressures, back pressures, fluid flow rates, and temperatures of the system. This data may later be used to determine, for example, a time interval at which a certain fluid loss control material began affecting the transmittance of fluids through either the fracture tip or through the matrix.

After collecting all necessary data, including measuring a fracture tip fluid loss and a matrix fluid loss, a sealing parameter is determined 405. Examples of sealing parameters that may be determined for a fluid include a seal location, an effective particle size, a fluid loss reduction, and/or a maximum sealing pressure. Those of ordinary skill in the art will appreciate that additional sealing parameters may also be determined that are based on, for example, viscosities of the fluid and/or sealing times.

In one embodiment, a seal location may be a sealing parameter that is determined during and/or after testing the drilling fluid. In such an embodiment, fracture closure pressures, as described above, are adjusted to balance increasing fluid sealing pressure and for the constant pressures to both the matrix and fracture tip. Thus, for force equilibrium conditions to exist, the fracture closure pressure must balance the contributions of the fluid pressure within the fracture and that of the fluid pressure behind the developing fracture seal.

Such a process means that from the measured pressure responses, the location of the fracture seal may by calculated using Eq. 1, an equation derived from the relationship between force and pressure:

$$r_1 = \sqrt{\frac{r_2^2(P_F - P_2)}{P_1 - P_2}} \quad \text{(Eq. 1)}$$

Where $P_F$ is the fracture "closure" pressure acting to hold the fracture closed, $P_1$ is the mud pressure acting on the wellbore side of the fracture seal, $P_2$ is the fluid (pore) pressure acting on the formation side of the fracture seal, $r_1$ is the radial distance from the center to the fracture seal, $r_2$ is the radial distance from the center to the outer edge of the sample/cell.

This force balance allows the capability of calculating the location of any seal. It also offers the ability to size a fluid loss control material for sealing either closer to the tip or nearer the mouth of the fracture as required for a given drilling operation. Thus, the ability to estimate a fracture seal location may allow for the optimization of a fluid loss control material according to the requirements for drilling a specific formation.

In other embodiments, a determined sealing parameter may include determination of a particle size of a fluid loss control material. Once the fracture seal location is determined, as described above, a particle size may be optimized to optimally control the flow of fluids through a formation of a known porosity. Additionally, the particle size may be adjusted to compensate for matrix fluid loss into a permeable formation. Thus, in the optimization of a drilling fluid, both the sealing properties of a drilling fluid for a fractured formation and a permeable formation may be compensated for by adjusting fluid loss control material particle size appropriately.

Those of ordinary skill in the art will appreciate that the particle size adjustments may provide a drilling operator the ability to reduce fluid loss to a specified level and determine a sealing pressure appropriate for a known formation, fluid, particle size, or other drilling parameter. Furthermore, the sealing parameters described herein are merely exemplary, additional conditions may be modeled by embodiments of the present disclosure to further analyze fracture size and leak-off rates (both to a fracture tip and matrix).

Still referring to FIG. 4, after a sealing parameter is determined, an operator may conclude the test by outputting and/or visually representing 406 the collected data and/or determined sealing parameters. Specific aspects of the visual representation will be discussed in greater detail below with regard to the Examples discussed herein. Generally, however, a visual representation may include numerical, graphical, or pictoral representations of the collected and/or determined data. Such representations may be output to a computer screen, printed on paper, or otherwise stored in a database for further analysis.

In certain embodiments, an operator may decide after determining 405 a sealing parameter that the fluid could be optimized by changing a variable in the drilling fluid. Thus, the operator may adjust 407 a parameter of the fluid and re-run the test. Examples of parameters that the operator may adjust include a viscosity, a flow-rate, a pressure, a back pressure, a fluid loss control fluid particle size, adding additional fluid loss control fluids, or changing other parameters of the system as would be known to those of skill in the art.

After a parameter of the fluid is adjusted 407, in this embodiment a particle size of a fluid loss control material, the test may be restarted by repeating the injecting 401 and/or 402, the measuring 403, 404, and determining 405 until the fluid is optimized 408. Optimization depends on the conditions an operator may be trying to achieve, however, examples of optimization may include when a drilling fluid seals within a given time interval, under a certain pressure, or under a certain fluid flow rate. Additionally, optimization may include optimizing a specified sealing parameter. Thus, in some embodiments, a fluid loss control material particle size may be optimized for a specified fracture width or in consideration of specific formation porosity.

EXAMPLES

The following examples were used to test drilling fluids with fluid loss control particles according to the methods and systems disclosed herein:

Example 1

Fracture tests using the systems and methods disclosed herein were focused to determine, inter alia, the sealing performance of solids-laden drilling fluids, with invert systems dominating the test matrix. Data was evaluated with respect to maximum sealing pressures, fracture size, leak-off rates (fracture tip and matrix), and particle size and seal location. Additional fluid-loss tests were also conducted on the fluids.

Under typical test conditions starting pressures of 3.5 MPa (approximately 500 psi) were used throughout the test at a flow rate of 10 mL/min. Fracture widths ranged from 250 to 1000 microns. The testing followed in accordance to the methods of testing fluids described in detail above. Briefly, a base fluid was used to pressurize the system of FIG. 1 by actuating a first pump. After pressurizing the system, a test fluid was pumped from a fluid container to a vessel having two opposed media plate disposed therein with a variable gap representative of a fracture therebetween. The test fluid continued to flow through the vessel allowing fracture tip fluid to exit the vessel by flowing into a collection container while matrix fluid loss flowed out of the vessel into a filtrate container. During the test, the pressures, temperatures, and other variables effecting the test were recorded by a data acquisition system and transmitted to a computer. The computer then compiled the data and measured a fracture tip fluid loss, a matrix fluid loss, a fluid pressure, a back pressure, an average seal radius, a filtrate volume, a fluids volume and fracture width. This data was then visually represented as a graph and displayed as described below.

Figure 5:
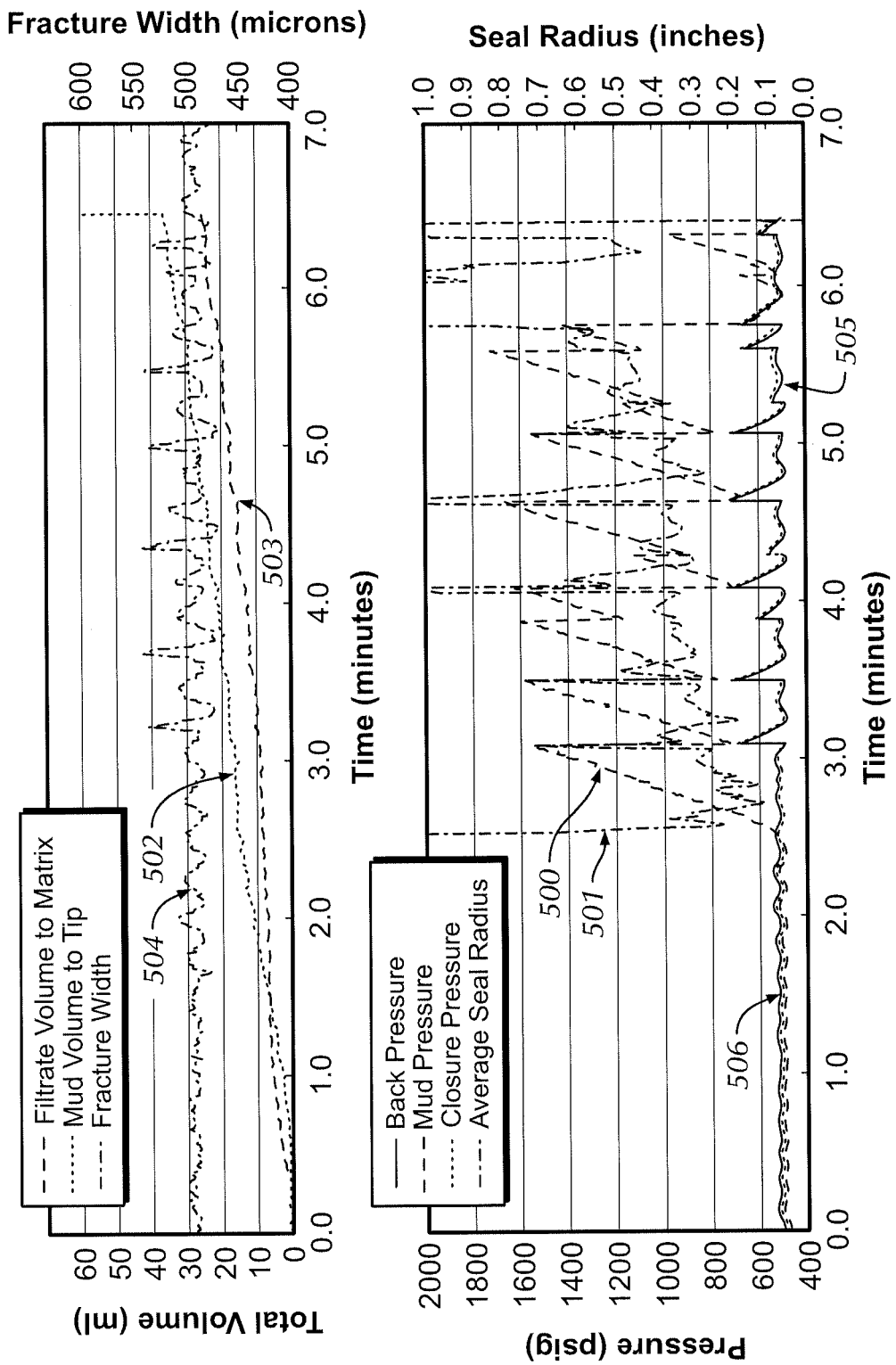
FIG. 5 shows a visual representation of permeable fracture test data generated according to embodiments of the present disclosure.

Referring to FIG. 5, a visual representation of a the data collected during a test of a fluid in accordance with embodiments of the present disclosure is shown. The following test includes an analysis of test fluid pressure ("mud pressure") 500, mud volume to tip ("conductivity loss") 502, conductivity loss to matrix 503, fracture width 504, average seal radius ("fracture seal location") 501, and back pressure 505 and fracture closure pressures 506.

Mud pressure 500 may be interpreted as the sealing pressure on the wellbore side of the fracture, As a bridge is formed, mud pressure 500 increases, Fluid pressure may continue to increase until a maximum of approximately 6000 psi, or the maximum operating pressure limit is met. Regarding conductivity 502 and 503, the values of each increases steadily with time as whole mud is lost to the fracture, Once an initial bridge forms, load-off is reduced and the slope of the line should flatten out. This reduction in slope corresponds to the building of a fracture seal and with it a corresponding reduction in fluid lost to the fracture. Referring to the fracture width, 504, as the test fluid pressure builds, and while the fracture seal formed remains in place, the fracture width is held steady (within design parameters) until the seal breaks. A break is indicated by a drop in fluid pressure combined with a minor increase in fracture width as the pumps compensate. Upon failure, fracture width 504 returns to the initial point and the mud pressure begins to rise again as a new seal forms. Fracture seal location 501 was calculated using Eq. 1, as described above. In this example, as consecutive seals fail, it would appear that the lost circulation material in the test fluid was pushed further into the fracture.

However, to further analyze the fracture testing of embodiments of the present disclosure, additional tests were completed using the same fluids and fluid loss control materials. To complement the fracture testing described above, High-Temperature, High-Pressure ("HTHP") fluid-loss tests were performed using standard API grade hardened filter paper at 148° C. and 3.5 MPa differential pressure. Additionally, Permeability Plugging Tests (PPT) tests were conducted under similar conditions with cut soapstone as a media replacing aloxite discs.

In such subsequent tests, both aqueous and non-aqueous fluids were used to evaluate the fracture sealing performance of a number of fluid loss control material blends and fluid-loss control additives at a multiple aperture widths using permeable substrate. The fluids were designed to give similar yield points of 10-15 to prevent solids settling within the device. A fluid density of 13 lb/gal, or 1.56 SG, was used throughout unless otherwise indicated. Types of fluids tested includes oil-based muds ("OBM"), water-based muds ("WBM"), and synthetic-based muds ("SBM"). The rheological properties are detailed below in Table 1:

TABLE 1

| Mud System | SBM 2 | SBM 1 | OBM 1 | WBM 1 (Optimized YP) | WBM 2 (Optimized Low End) | SBM 3 | SBM 4 |
| --- | --- | --- | --- | --- | --- | --- | --- |
| Mud Weight (ppg) | 13 | 13 | 13 | 13 | 13 | 9.5 | 18 |
| Rheology/° F. | 150 | 150 | 150 | 120 | 120 | 150 | 150 |
| 600 rpm | 42 | 52 | 61 | 95 | 121 | 36 | 75 |
| 300 rpm | 27 | 34 | 38 | 55 | 75 | 25 | 45 |
| 200 rpm | 23 | 30 | 30 | 42 | 57 | 19 | 35 |
| 100 rpm | 15 | 22 | 20 | 25 | 36 | 14 | 25 |
| 6 rpm | 6 | 10 | 7 | 4 | 8 | 7 | 10 |
| 3 rpm | 5 | 9 | 6 | 3 | 6 | 6 | 9 |
| PV | 15 | 18 | 23 | 40 | 46 | 11 | 30 |
| YP | 12 | 16 | 15 | 15 | 29 | 14 | 15 |
| 10 sec | 7 | 11 | 10 | 3 | 7 | 7 | 10 |
| 10 min | 8 | 13 | 13 | 4 | 9 | 8 | 12 |
| ES (volts) | 1247 | 484 | 1125 | N/A | N/A | 703 | 1179 |

The selection of loss control materials for use in this study was based in large part on the findings from the previous fracture studies. Calcium carbonate, graphite, and cellulosic nut shells, of specific particle sizes, were all tested. Combinations of these materials were used in conjunction with an appropriate fluid-loss reducer, either gilsonite or resin base for the inverts, denoted "G" and "R" respectively.

To assess the effects of fluid loss on fracture sealing, a number of HTHP and PPT fluid-loss tests were performed at 148° C. and 3.5 MPa differential pressure. The fluid-loss and PSD properties of non-aqueous fluids used in fracture tests are detailed in Table 2:

TABLE 2

| Test No. | LCM Additives (lb/bbl) | d50 (mud) PSD Range (LCM) | Mud System | Fluid Loss Additive | Fluid Loss Additive (lb/bbl) | HTHP (ml) | Filter Cake (mm) | PPT Spurt Loss (g) | PPT Total Loss (g) |
|---|---|---|---|---|---|---|---|---|---|
| 1 | CaCO3 B (27) + Graphite A (13) | +/− 30 μm +/− 450 μm | SBM 1 | R | 2 | 7 | 6.1 | 22.6 | 26.9 |
| 2 | Nut (10) + Graphite B (10) | +/− 50 μm +/− 800 μm | SBM 1 | R | 2 | 8.4 | 4.9 | 40.1 | 43.1 |
| 3 | Graphite B (20) | − +/− 550 μm | SBM 1 | R | 2 | 8.6 | 4.7 | 36.5 | 36.7 |
| 4 | CaCO3 A (27) + Graphite A (13) | +/− 15 μm +/− 400 μm | SBM 1 | R | 2 | 9 | 6.1 | 45.3 | 46.4 |
| 5 | Nut (20) + Graphite B (20) | − +/− 800 μm | SBM 1 | N/A | 0 | 10 | 6.3 | 22.2 | 26.6 |
| 6 | − | − − | SBM 1 | N/A | 0 | 10.4 | 5.5 | 67.1 | 70.6 |
| 7 | − | +/− 10 μm − | SBM 1 | R | 2 | 10.6 | 6.2 | 94.7 | 94.9 |
| 8 | Nut (20) + Graphite B (20) | − +/− 800 μm | SBM 1 | R | 2 | 11 | 8.2 | 24.3 | 29.3 |
| 9 | Graphite B (20) | − +/− 550 μm | OBM 1 | R | 2 | 19.8 | 13.8 | 35.8 | 53.4 |
| 10 | − | − − | OBM 1 | R | 2 | 19.8 | 11.7 | 253 | NC |
| 11 | Nut (20) + Graphite B (20) | − +/− 800 μm | SBM 2 | G | 5.25 | 30 | 10.4 | 22.5 | 24.4 |

The conductivity loss and fracture sealing properties of non-aqueous fluids are detailed in Table 3:

TABLE 3

| Test # | Fx Width (um) | Loss to: | Conductivity up to formation of Initial Seal (mL) Lower is Better | Total Conductivity up to formation of Initial Seal (mL) | Conductivity after formation of Initial Seal (mL) Lower is Better | Total Conductivity after formation of Initial Seal (mL) | Time to Seal (min) | Fracture Sealing Pressure (psig) | Radial Distance from Center Line (in.) |
|---|---|---|---|---|---|---|---|---|---|
| 1 | 500 | filtrate tip | 9.7 17.8 | 27.4 | 1.9 4.9 | 6.7 | 0.3 | 1547 | 0.28 |
| 2 | 500 | filtrate tip | 7.7 30.6 | 38.3 | 4.9 14.6 | 19.5 | 0.6 | 6132 | 0.20 |
| 3 | 500 | filtrate tip | 9.6 26.6 | 36.3 | 3.9 10.1 | 13.9 | 1.1 | 1962 | 0.28 |
| 4 | 500 | filtrate tip | 11.4 55.6 | 67.0 | 8.8 36.7 | 45.5 | 7.0 | 988 | 0.37 |
| 5 | 1000 | filtrate tip | 5.6 21.2 | 26.8 | 1.3 1.2 | 2.5 | 0.1 | 3611 | 0.15 |
| 6 | 250 | filtrate tip | 89.2 44.9 | 134.1 | 47.6 30.5 | 78.1 | 12.5 | 1746 | 0.31 |
| 7 | 250 | filtrate tip | 19.0 53.0 | 72.0 | 17.0 36.3 | 53.3 | 8.4 | 2733 | 0.35 |
| 8 | 1000 | filtrate tip | 2.7 28.6 | 31.3 | 0.2 11.4 | 11.7 | 1.1 | 2037 | 0.12 |
| 9 | 500 | filtrate tip | 12.4 14.3 | 26.6 | 3.8 5.0 | 8.8 | 2.4 | 3836 | 0.17 |
| 10 | 250 | filtrate tip | 1.7 85.8 | 87.5 | 1.0 65.5 | 66.5 | 5.5 | 679 | 0.30 |
| 11 | 1000 | filtrate tip | 1.3 25.4 | 26.6 | 0.4 1.5 | 1.8 | 2.6 | 4420 | 0.13 |

As illustrated in Table 2, the HTHP tests exhibit lower fluid-loss values when smaller particle-sized materials are used. It would also appear that HTHP values do not correlate with PPT performance using soapstone plates. Both sets were then evaluated with respect to the permeable fracture test results to determine if either of these two analysis methods could provide an indication of relative performance in sealing a fractured permeable zone with a given formation permeability.

Figure 6:
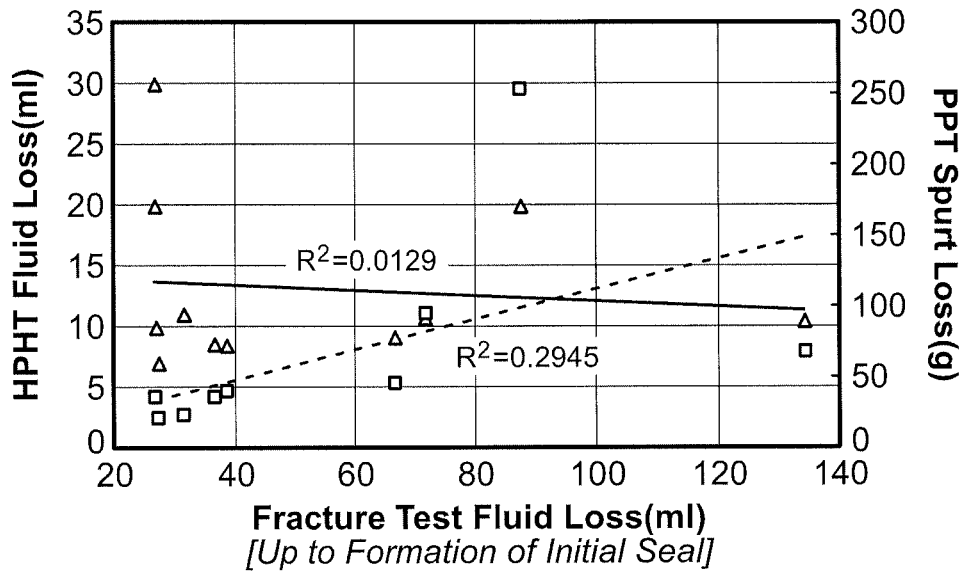
FIGS. 6 and 7 show fluid-loss values referenced against fracture test data according to embodiments of the present disclosure.
Figure 7:
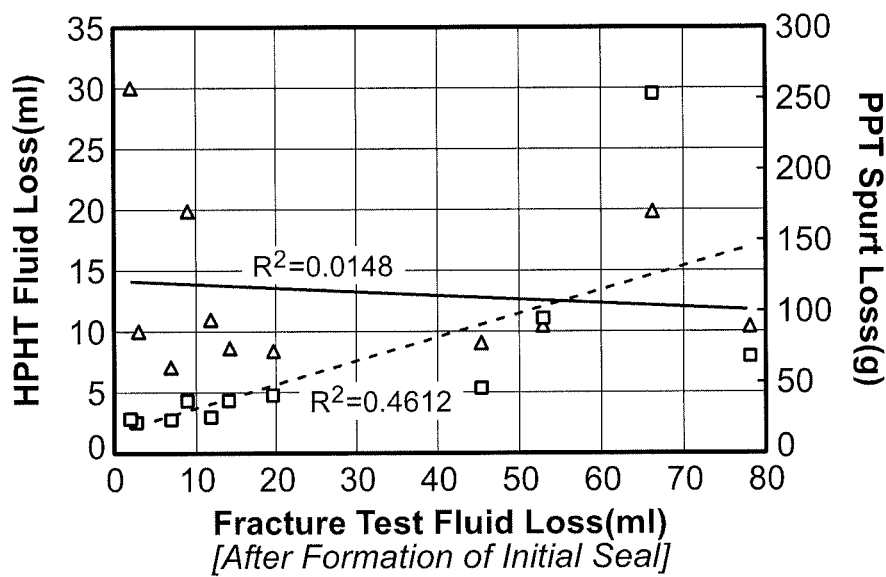

Referring to FIGS. 6 and 7 together, a graphical representation of data gathered in HTHP and PPT tests is shown. In these figures, HTHP and PPT data from Table 3 able are plotted with respect to total fracture fluid-loss both before and after the seal begins to develop. In the PPT and HTHP tests, particle plugging occurs on a pre-existing surface (i.e., the soapstone or hardened filter paper). For the fracture test, the equivalent boundary condition is the point where a foundation layer of particles that brides the fracture aperture has developed. Prior to this point, fluid loss will be domination by the open portion of the fracture based on the principle of the path of least flow resistance. Once a foundation layer is established then a filter cake, based on conventional plugging principals, may evolve with fluid loss giving an indication of how tightly the particles fit together.

As illustrated in FIGS. 6 and 7, there is a moderate correlation between fluid spurt loss measure using PPT and that measured in the fracture tests. The correlation is strongest for low fluid loss values where theses test points tend to have higher sealing pressures.

The similarity between the PPT and fracture sealing data demonstrates that reducing fluid loss is an interplay between pore plugging mechanisms and the substrate on which the filter cake forms, in this case, the soapstone surface and the particle bridge that forms the foundation of the fracture seal. Furthermore, for the case of high permeability/high porosity substrate, relatively coarse loss control materials blends are the most effective methods to reduce this spurt loss.

Those of ordinary skill in the art will appreciate that the above described example is only one such outcome of a test using systems and methods in accordance with the present disclosure. In other embodiments, the test may include additional visual representations of data and/or data sets compiled by a data acquisition system or computer, and may include a detailed analysis of varied properties of fluid loss control materials. Examples of such visual representations and/or studies that may be generated using systems and methods of the present disclosure include a comparison of permeable fracture tests at varying fluid densities, as represented in FIG. 8.

Figure 8:
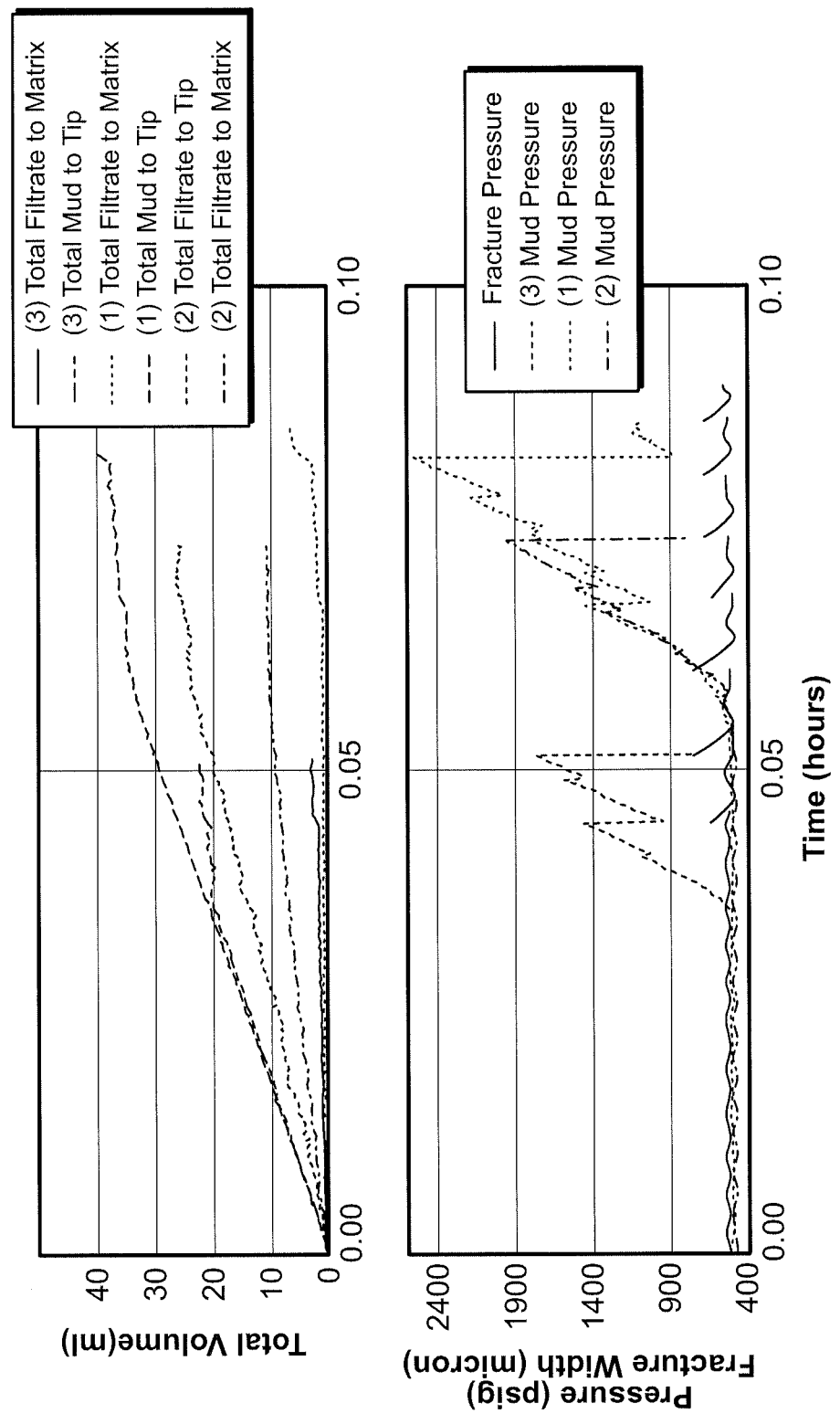
FIG. 8 shows a visual representation of permeable fracture test data generated according to embodiments of the present disclosure.

FIG. 8 illustrates a fracture evaluation by increasing the density of the fluid, wherein the fracture is 500 microns, the flowrate is 10 mL/min, there is a substantially constant 500 psi pore pressure. The evolution of the test includes increasing the fluid density in steps including 1.14 SG, 2.56 SG, and 2.14 SG. Those of ordinary skill in the art will appreciate that the aforementioned illustrated and described tests may be altered in accordance with the methods described herein to test a plurality of sealing parameters and/or otherwise evaluate the sealing characteristics of drilling fluids and fluid loss control materials.

Advantageously, embodiments of the present disclosure may provide systems and methods for testing and evaluating drilling fluids and fluid loss control materials. Embodiments disclosure herein may advantageously provide methods for assessing the effectiveness of fluid loss control materials in sealing permeable and/or impermeable fractures. Furthermore, the system and methods may inexpensively and rapidly test the sealing effectiveness of various fluid loss control materials as well as provide a way to control and measure changes in fracture width in formation.

Also advantageously, the systems and methods disclosed herein may allow an operator to optimize fluid loss control materials types and concentrations for specific fracture widths, as well as providing an indication of propped width within sealed fractures caused by fluid loss control materials that have been pressed into the fractured. Finally, embodiments of the present disclosure may allow an operator to test and optimize drilling fluids and fluid loss control materials under higher pressures with greater precision. Such tests may further provide an operator the ability to measure two discrete fluid streams, specifically, through the fracture tip and formation matrix, to optimize drilling fluids for drilling in permeable and/or fractured formation.

While the present disclosure has been described with respect to a limited number of embodiments, those skilled in the art, having benefit of the present disclosure will appreciate that other embodiments may be devised which do not depart from the scope of the disclosure described herein. Accordingly, the scope of the disclosure should be limited only by the claims appended hereto.

What is claimed is:

1. A method comprising:
    injecting a test fluid having a fluid loss control material from a test fluid container to a vessel, the vessel comprising:
        two media plates;
        wherein the two media plates are disposed to create a variable gap therebetween;
    measuring a first amount of fluid that flows through the variable gap from an injection location to a first outlet; and
    measuring a second amount of fluid that permeates at least one of the two media plates to a second outlet.

2. The method of claim 1, further comprising:
    determining a first sealing parameter based on the first amount of fluid.

3. The method of claim 2, wherein the determining the first sealing parameter comprises determining at least one of a seal location, particle size, reduction of fluid loss, and maximum sealing pressure.

4. The method of claim 2, further comprising:
    determining a second sealing parameter based on the second amount of fluid.

5. The method of claim 4, wherein the determining the second sealing parameter comprises determining at least one of a seal location, particle size, reduction of fluid loss, and maximum sealing pressure.

6. The method of claim 4, further comprising:
    visually representing at least one of a group consisting of the first amount of fluid, the second amount of fluid, the first sealing parameter, and the second sealing parameter.

7. The method of claim 1, further comprising:
    determining a sealing parameter based on a volume of the first amount of fluid and a volume of the second amount of fluid and
    adjusting the particle size based on the sealing parameter.

8. The method of claim 7, further comprising:
    injecting the drilling fluid having the adjusted particle size into the vessel; and
    repeating the measuring the first amount of fluid, measuring the second amount of fluid, determining, adjusting, and injecting the drilling fluid having the adjusted particle size until the material particle size of the drilling fluid is optimized.

9. The method of claim 7, wherein the sealing parameter is at least one of a seal location, particle size, reduction of fluid loss, and maximum sealing pressure.

10. A method for testing a drilling fluid comprising:
    pressurizing a system for testing a drilling fluid, the system including a vessel, at least one pump, and a fluid container;
    pumping a test fluid from the fluid container into the vessel comprising two media plates defining a variable gap approximating a fracture width between the plates;
    flowing the test fluid through the variable gap to produce a fracture tip loss fluid;
    flowing the test fluid through at least one of the two media plates to produce a matrix fluid loss fluid; and
    determining a sealing parameter based on the fracture tip fluid loss and matrix fluid loss fluids, wherein the determining the sealing parameter comprises determining at least one of a seal location, particle size, reduction of fluid loss, and maximum sealing pressure.

11. The method of claim 10, further comprising:
    recording data of at least one of fluid pressure, fracture tip fluid loss, matrix fluid loss, fracture width, average seal radius, back pressure, and fracture closure pressure with a data acquisition center;
    transmitting the data from the data acquisition center to a computer; and
    compiling the data and producing a visual representation of the data.

12. The method of claim 11, wherein the system for testing a drilling fluid further comprises at least one sensor operatively coupled to the data acquisition center.

13. The method of claim 12, further comprising sending instructions from the computer to at least one of the data acquisition center, the at least one sensor, and the at least one pump.

14. The method of claim 13, wherein the instructions are configured to control at least one of a pressure, a flow rate of the test fluid, a distance between media plates, or instructions to request additional data from at least one of the data acquisition center, the at least one sensor, and the at least one pump.

15. The method of claim 10, further comprising maintaining a constant width of the variable gap.

16. The method of claim 15, wherein the variable gap has a tapered configuration.

* * * * *